United States Patent [19]

Kitamori et al.

[11] Patent Number: 4,702,919
[45] Date of Patent: Oct. 27, 1987

[54] GRANULES OF THIAMINE SALT AND THE PRODUCTION THEREOF

[75] Inventors: Nobuyuki Kitamori; Masaya Maeno, both of Suita; Seiji Izuhara, Tondabayashi, all of Japan

[73] Assignee: Takeda Chemical Industries, Ltd., Osaka, Japan

[21] Appl. No.: 785,391

[22] Filed: Oct. 8, 1985

[30] Foreign Application Priority Data

Oct. 9, 1984 [JP] Japan ................................ 59-212345

[51] Int. Cl.$^4$ .......................... A61K 9/36; A61K 9/16; A61K 31/51
[52] U.S. Cl. .................................... 424/480; 424/474; 424/490; 424/494; 514/276
[58] Field of Search .................... 514/276; 424/31, 35, 424/480, 474, 494, 490

[56] References Cited

U.S. PATENT DOCUMENTS 2,540,253  2/1951  Gakenheimer ...................... 514/276
3,907,983  9/1975  Seth ........................................ 424/35
4,036,948  7/1977  Kitamori et al. ...................... 424/32
4,372,968  2/1983  Kitamori et al. ...................... 514/474
4,486,435 12/1984  Schmidt et al. ...................... 514/276

FOREIGN PATENT DOCUMENTS 49-46046  7/1974  Japan ................................ 514/276

Primary Examiner—Ronald W. Griffin
Attorney, Agent, or Firm—Wenderoth, Lind & Ponack

[57] ABSTRACT

Granules consisting of a thiamine salt and a binder such as water-soluble celluloses, said thiamine salt accounting for about 95 to about 98 percent by weight on the dried basis, can be prepared by spray-coating thiamine salt powder at least about 95 percent by weight of which is capable of passing through a 145-mesh sieve with a solution containing a binder while maintaining said thiamine salt powder in a fluidized state in a fluidized-bed granulation apparatus. The granules are excellent in flowability, mixability, compressibility and bonding properties, and can be used for tablet manufacturing.

10 Claims, No Drawings

GRANULES OF THIAMINE SALT AND THE PRODUCTION THEREOF

This invention relates to thiamine (vitamin $B_1$) salt granules and to a method for producing the same.

A thiamine (vitamin $B_1$) salt is administered either alone or together with other vitamins and/or some other drug substance, generally in the form of tablets. Such tablets are generally produced by compressing thiamine salt-containing powder either directly or after granulation.

The process for tablet manufacture would become fairly simple from the labor viewpoint if such powder could be compressed directly without preliminary granulation. However, thiamine salts are poor in flowability and compressibility, which are characteristics necessary for compression and it is impossible to form thiamine salt powder directly into tablets. For these reasons, thiamine salts are generally mixed with other vitamins or active drug substances and/or excipients, followed by wet granulation or kneading methods and tableting.

A conventional wet granulation as mentioned above can hardly afford homogeneous thiamine salt granules. Granules obtained by such kneading methods are not very good in flowability. Tablets made of said granules are not satisfactory in mechanical strength. Moreover, granules obtained by an ordinary wet granulation demand a large amount of excipient in the tableting step and this leads to a great increase in the tablet weight resulting in difficulty in taking the tablet.

The present inventors conducted investigations in order to overcome the drawbacks mentioned above and found that the granulation of thiamine salt powder in a fluidized-bed granulation apparatus using a small amount of a binder can produce granules capable of being tableted with a small quantity of an excipient, and the granules give tablets having a satisfactorily high hardness. As a result of continued investigations based on this finding, the inventors have now completed the present invention.

The invention thus deals with:

(1) Thiamine salt granules consisting essentially of a thiamine salt and a binder, said thiamine salt accounting for about 95 to about 98 percent by weight of the granules on a dry basis;

(2) A method for producing thiamine salt granules which comprises spray-coating thiamine salt powder at least about 95 percent by weight of which is capable of passing through a 145-mesh (JIS) sieve with a solution containing a binder in an amount corresponding to about 2 to about 5 percent by weight based on the whole granular product weight (dried basis) while maintaining said thiamine salt powder in a fluidized state in a fluidized-bed granulation apparatus; and (3) Thiamine salt-containing tablets obtained by compressing a tableting mixture containing granules essentially consisting of a thiamine salt and a binder, said thiamine salt accounting for about 95 to about 98 percent by weight of said granules on the dried basis.

The thiamine salt to be used in the practice of the invention is, for example, thiamine nitrate and thiamine hydrochloride.

The thiamine salt is used in the form of a powder at least about 95 percent by weight of which is capable of passing through a 145-mesh (JIS) sieve. The powder is preferably such that all particles can pass through a 145-mesh (JIS) sieve and at least about 50 percent by weight of the powder can pass through a 280-mesh (JIS) sieve.

The fluidized-bed granulation apparatus is a fluidized-bed drying apparatus equipped with binder spraying means, in which granulation and drying can be carried out. As such apparatus, there may be mentioned models available on the market under the names Glatt (made by Glatt AG in West Germany and Okawara Seisakusho Co. in Japan), Aeromatic (made by Aeromatic AG in Switzerland and Fuji Industries Co. in Japan), Calmic (made by Calmic Engineering Co. in Great Britain), Growmax (made by Fuji Powdal Co. in Japan) and Flowcoater (Freund Industries Co. in Japan).

As the binder to be contained in the solution for spray-coating, there is used a water-soluble binder or an organic solvent-soluble binder.

The water-soluble binder includes pregelatinized starches, water-soluble celluloses and water-soluble macromolecules. A pregelatinized starch is a product obtained, for example, by heating a dispersion of starch in water, followed, as desired, by drying. Examples of the pregelatinized starch are pregelatinized corn starch, pregelatinized potato starch and pregelatinized modified starches (e.g. those described in the Code of Federal Regulations (U.S.A.), Title 21, Section 121.1031, Paragraphs a, b, c, d, e, f, g and h). There may also be used those pregelatinized and dried starches which are commercially available under the trademarks Amicol C (manufactured by Nichiden Chemical Co. in Japan), Pre-Gel (manufactured by Hublinger Co. in U.S.A.), Instant Cleargel (manufactured by National Starch Co. in U.S.A.), etc.

The water-soluble celluose includes hydroxypropylcellulose, hydroxymethylcellulose, hydroxypropylmethylcellulose, carboxymethylcellulose and methylcellulose. The water-soluble macromolecule includes polyvinylpyrrolidone(M.W. 10,000–100,000), polyvinyl alcohol (M.W. 10,000–50,000), dextrin, gum arabic and gelatin.

The organic solvent-soluble binder is, for example, an organic solvent-soluble cellulose derivative (e.g. cellulose acetate phthalate, hydroxypropylmethylcellulose phthalate, ethylcellulose). Among them, the water-soluble binder, especially water-soluble celluloses are preferably used.

As the solvent for dissolving the binder in preparing a binder solution for spraying, there may be mentioned solvents capable of dissolving the above-mentioned binder, such as water and an organic solvent such as alcohols (e.g. methyl alcohol, ethyl alcohol, isopropyl alcohol) and ketones (e.g. acetone).

The binder concentration is, for instance, a concentration of about 1 to 10 percent by weight, preferably about 2 to about 8 percent by weight of the binder solution. The practical concentration varies with the binder-solvent combination employed, but is favorably such as to give a viscosity of about 1 to about 1,000 centipoise, preferably about 10 to about 500 centipoise which is necessary for spraying. The granulation is carried out by spray-coating thiamine salt powder with a solution containing a binder, while allowing the powder to fluidize in a fluidized-bed granulation apparatus until the amount of the binder has reached about 2 to about 5 weight percent relative to the granules. To allow the powder to fluidize, heated air up to about 100° C., preferably about 80 to 90° C. can be used. The exhausted gas temperature is normally maintained at around 30 to 60° C.

After granulation, drying is carried out in a conventional manner. Thus, after completion of spraying, fluidizing air alone is fed until the bed temperature reaches a predetermined temperature, for example 30° C. to 60° C., whereby drying can be achieved.

The dried matter is already a granular composition. If desired, however, it can be passed through a mill, such as a Power mill or a Fits mill, in order to crush some aggregates to get a more desirable grain size distribution.

The method as described produces granules which consist essentially of a thiamine salt and a binder, with the thiamine salt accounting for about 95 to about 98 percent by weight on the dried basis. A desirable grain size is such that the portion of grains which do not pass through a 32-mesh (JIS) sieve accounts for not more than 5 percent by weight and that portion of grains which pass through a 145-mesh (JIS) sieve accounts for not more than 30 percent by weight. An excessively coarse granular composition is unsuited for admixture with some other granular composition and moreover causes weight fluctuation in tablet manufacture. An excessively fine composition is also undesirable because of its poor flowability in charging into dies in tableting.

The thiamine salt granules according to the invention can be used as a raw material in the manufacture of thiamine salt-containing tablets.

Tableting of the granules is carried out by a conventional method in the presence of a lubricant and, if necessary, some other drug substance and/or an excipient (e.g. lactose, sucrose, mannitol). As said lubricant, there may be mentioned those lubricants which are used in conventional tablet manufacture, such as stearic acid and stearates (e.g. magnesium stearate, calcium stearate) and talc. The amount and kind of the lubricant are selected within such a range as to give tablets which are practical from the strength and disintegration viewpoint. Recommendably it is used generally in an amount of about 0.1 to about 7 percent by weight based on the main active substance. Of the lubricants, a stearate or stearic acid is desirably added in an amount of at least about 0.5 percent by weight based on the main active substance. The above-mentioned other drug substance includes L-ascorbic acid and sodium L-ascorbate. The L-ascorbic acid and sodium L-ascorbate each is preferably used in the form of granules obtained by spray-coating the same with a binder in a fluidized-bed granulation apparatus (refer to U.S. Pat. Nos. 4,036,948 and 4,372,968). The mixing ratio with the other drug substance is not critical. For instance, when a mixture of the granular composition of the present invention with L-ascorbic acid or sodium L-ascorbate is compressed into tablets, L-ascorbic acid or sodium L-ascorbate is used in an amount of about 10 to about 30 parts by weight per part by weight of the thiamine salt. The compression is normally carried out under the condition of 1 to 2 ton/cm$^2$.

In accordance with the method of the invention, there can be obtained thiamine salt granules of thiamine salt powder uniformly coated with a small amount of a binder. The granules can be compressed into tablets containing the high concentration of thiamine salt only by a simple procedure comprising mixing the granules with a lubricant and other ingredients and tableting the mixture. The granules do not contain fine powder and have good flowability. These characteristics are favorable as a raw material for direct compression, and also convenient for handling, and scarcely lead to dust rising. The granules have good mixability with other ingredients or granules. The granules of the invention, though having a very low binder content, have good stability even after mixing with other ingredients or granules, show good bonding property, and have good compressibility, because the surface of the thiamine salt particles is uniformly coated. Accordingly, a small excipient amount is sufficient for tablet manufacture and the tablet size can be reduced. Owing to these characteristics, the granules are very suited for the manufacture of multivitamin preparations, in which the stability of thiamine salt is assured in a separated state from other vitamins. The hardness of the whole tablet can be secured by the use of the granules with good bonding properties.

An excipient to be used is sufficient in a small amount not only for tablets containing a thiamine salt alone as active ingredient but also for tablets containing a thiamine salt in combination with other drug substances. The use of the granules can result in a reduced tablet size. The tablets obtained have satisfactory mechanical strength and other preferable properties such as rapid disintegration. Therefore, the tablets from the granules according to the present invention can be taken easily. Furthermore, the granules according to the invention have the advantage that they are considerably reduced in odor peculiar to vitamin $B_1$.

The mesh sizes as defined in this specification are those specified in the relevant Japanese Industrial Standard (JIS). Said mesh sizes and the corresponding sieve opening sizes are shown below.

| Mesh | Sieve opening size ($\mu$) |
| --- | --- |
| 32 | 500 |
| 145 | 105 |
| 200 | 77 |
| 280 | 53 |
| 325 | 44 |

EXAMPLES

The following examples are further illustrative of the present invention. In the following, "part(s)'8 means part(s) by weight.

Example 1

A fluidized-bed granulation apparatus was charged with 97 parts of thiamine nitrate powder capable of passing through a 200-mesh (JIS) sieve. The powder was fluidized and was sprayed with a starch paste which had been prepared in advance by dispersing corn starch in water to make a concentration of 6 percent by weight and by gelatinizing at 75° C. The spraying was stopped when the spraying amount reached an amount corresponding to 3 parts on the solid basis, followed by drying in the apparatus. The granular mass thus obtained was passed through a Fitz mill with a 1.0-mm screen to give thiamine nitrate-containing granules. As for the grain size, 3.1 percent of the granules remained on a 32-mesh (JIS) sieve and 11.4 percent passed through a 145-mesh (JIS) sieve.

Example 2

The procedures of Example 1 were followed except that a 5 weight percent aqueous solution of hydroxypropylmethylcellulose was used as the binder solution. The granules thus obtained showed the following grain size: 2.7 percent remained on a 32-mesh (JIS) sieve and 10.6 percent passed through a 145-mesh (JIS) sieve.

Example 3

In a fluidized-bed granulation apparatus, 97.5 parts of thiamine hydrochloride powder capable of passing through a 200-mesh (JIS) sieve and further capable, by 58.3 percent by weight, of passing through a 325-mesh (JIS) sieve was fluidized and sprayed with an ethanol solution containing 4.0 percent by weight of ethylcellulose. When the amount of the spraying solution reached 2.5 parts as ethylcellulose, the spraying was discontinued and the fluidized mass was dried in situ under the fluidizing condition. There were obtained thiamine hydrochloride-containing granules, 1.8 percent of which remained on a 32-mesh (JIS) sieve and 22.5 percent of which passed through a 145-mesh (JIS) sieve.

Example 4

In a fluidized-bed granulation apparatus, 96.5 parts of thiamine hydrochloride powder capable of passing through a 200-mesh (JIS) sieve was fluidized and sprayed with a 5.0 weight percent aqueous solution of hydroxypropylcellulose. When the amount of the solution reached 3.5 parts as hydroxypropylcellulose, the spraying was discontinued and the fluidized mass was dried in the apparatus. The granulation product obtained was passed through a Power mill equipped with a 1.0-mm screen to give thiamine hydrochloride-containing granules. As for the grain size, 5.3 percent of the granules remained on a 32-mesh (JIS) sieve and 17.2 percent passed through a 145-mesh (JIS) sieve.

Example 5

In a fluidized bed-granulation apparatus, 96 parts of thiamine nitrate powder capable of passing through a 200-mesh (JIS) sieve and further capable, by 37.4 percent by weight, of passing through a 325-mesh (JIS) sieve was fluidized and sprayed with an 8 weight percent aqueous solution of polyvinylpyrrolidone until the weight of polyvinylpyrrolidone sprayed amounted to 3.5 parts, followed by drying in the apparatus. The thus-obtained granulation product was passed through a Power mill equipped with a 1.0-mm screen to give thiamine nitrate-containing granules. The grain size of the granules was such that 4.0 percent remained on a 32-mesh (JIS) sieve and 13.0 percent passed through a 145-mesh (JIS) sieve.

Reference Example

The granules obtained in Example 2 and the granules prepared by a conventional kneading method were subjected to a sensory test.

Thus, the two kinds of granules were stored in tightly closed glass bottles (each containing 100 g of either granules) at 25° C. for 1 week.

The sensory test on odor was performed by 10 volunteers in the manner of blind trial. Upon opening the bottles, the volunteers brought their nostrils close to the bottles and were asked if there was a difference in odor between both the granules. While one volunteer noticed no difference, nine answered there was a difference, all evaluating the granules obtained in Example 2 as having less odor. This result clearly indicated that the method of the present invention is more effective in suppressing emanation of the unpleasant odor peculiar to vitamin $B_1$ than the conventional method.

When compared with the thiamine nitrate crystals not yet made up into granules, the granules obtained in Example 2 were noticeably less odorous.

In preparing the granules for comparison by a conventional method, there was used the same formula as used for the granules of Example 2. Thus, a 20% aqueous solution of the binder, hydroxypropylmethylcellulose, was added to a thiamine nitrate powder charged in a Pony mixer, and the mixture was kneaded. The wet mixture was ground in a Power mill and then dried under vacuum at 40° C. for 16 hours. The dried mixture was ground again in a Power mill to give the final product granules.

Example 6

The thiamine nitrate-containing granules as obtained in Example 1 (103.1 parts) were admixed with 6.6 parts of corn starch and 0.3 part of magnesium stearate. The mixture was compressed into tablets each weighing 110 mg and having a diameter of 6.5 mm. Each tablet contained 100 mg of thiamine nitrate and had a hardness of 4.9 kg as measured with a Heberlein hardness tester. The disintegration time as measured by the Japanese Pharmacopeia method was 4.2 minutes.

Example 7

A mixture was prepared by mixing 25.8 parts of the thiamine nitrate-containing granules obtained in Example 2, 515.5 parts of the granules which had been prepared by coating L-ascorbic acid (97 parts) with an aqueous solution of hydroxypropylmethylcellulose (3 parts) in a fluidized-bed granulation apparatus as is disclosed in U.S. Pat. No. 4,036,948, 7.2 parts of crystalline cellulose and 1.5 parts of magnesium stearate. The mixture was compression-molded into tablets each weighing 550 mg. Each tablet had a diameter of 11 mm and contained 500 mg of L-ascorbic acid and 25 mg of thiamine nitrate. The hardness was measured with a Heberlern hardness tester to be 7.2 kg and the disintegration time was measured by the method of Japanese Pharmacopeia to be 7.3 minutes.

We claim:

1. Thiamine salt granules consisting essentially of a thiamine salt and a binder, said thiamine salt accounting for about 95 to about 98 percent by weight of said granules on a dry basis, said granules having a grain size such that the portion of grains which do not pass through a 32-mesh sieve accounts for not more than 5 percent by weight and the portion of grains which pass through a 145-mesh sieve accounts for not more than 30 percent by weight, which granules are produced by spray-coating thiamine salt powder at least about 95 percent by weight of which is capable of passing through a 145-mesh sieve, with a solution containing a binder in an amount corresponding to about 2 to about 5 percent by weight based on the weight of said granules while maintaining said thiamine salt powder in a fluidized state in a fluidized-bed granulation apparatus.

2. Granules as claimed in claim 1, wherein the powder to be spray-coated is such that all particles of the powder can pass through a 145-mesh sieve and at least about 50 percent by weight of the powder particles can pass through a 280-mesh sieve.

3. Granules as claimed in claim 1, wherein the binder is a water-soluble cellulose.

4. Granules as claimed in claim 3, wherein the water-soluble cellulose is hydroxypropylcellulose, hydroxymethylcellulose, hydroxypropylmethylcellulose, carboxymethylcellulose or methylcellulose.

5. A method for producing thiamine salt granules consisting essentially of a thiamine salt and a binder, said thiamine salt accounting for about 95 to about 98 percent by weight of said granules on a dry basis, said granules having a grain size such that the portion of grains which do not pass through a 32-mesh sieve accounts for not more than 5 percent by weight and the portion of grains which pass through a 145-mesh sieve accounts for not more than 30 precent by weight, which comprises spray-coating thiamine salt powder at least about 95 percent by weight of which is capable of passing through a 145-mesh sieve, with a solution containing a binder in an amount corresponding to about 2 to about 5 percent by weight based on the weight of said granules while maintaining said thiamine salt powder in a fluidized state in a fluidized-bed granulation apparatus.

6. A method as claimed in claim 5, wherein the powder to be spray-coated is such that all particles of the powder can pass through a 145-mesh sieve and at least about 50 percent by weight of the powder particles can pass through a 280-mesh sieve.

7. A method as claimed in claim 5, wherein the binder is a water-soluble cellulose.

8. A method as claimed in claim 5, wherein the concentration of the binder in the solution is about 1 to about 10 weight percent.

9. Thiamine salt-containing tablets obtained by compressing a tableting mixture containing granules consisting essentially of a thiamine salt and a binder, said thiamine salt accounting for about 95 to about 98 percent by weight of said granules on a dry basis, said granules having a grain size such that the portion of grains which do not pass through a 32-mesh sieve accounts for not more than 5 percent by weight and the portion of grains which pass through a 145-mesh sieve accounts for not more than 30 percent by weight, which granules are produced by spary-coating thiamine salt powder at least about 95 percent by weight of which is capable of passing through a 145-mesh sieve, with a solution containing a binder in an amount corresponding to about 2 to about 5 percent by weight based on the weight of said granules while maintaining said thiamine salt powder in a fluidized state in a fluidized-bed granulation apparatus.

10. Tablets as claimed in claim 9, wherein the powder to be spray-coated is such that all particles of the powder can pass through a 145-mesh sieve and at least about 50 percent by weight of the powder particles can pass through a 280-mesh sieve.

* * * * *